(12) United States Patent
Lu et al.

(10) Patent No.: US 9,042,970 B2
(45) Date of Patent: May 26, 2015

(54) METHOD AND SYSTEM FOR FACILITATING REMOTE MEDICAL DIAGNOSIS AND CONSULTATION

(76) Inventors: Ying-Chiang Lu, Singapore (SG); Kae Yuan Tan, Singapore (SG); Saravanan Sundaramoorthy, Singapore (SG); Lanzi Jiang, Singapore (SG); Xiong Kai Teo, Singapore (SG)

(*) Notice: Subject to any disclaimer, the term of this patent is extended or adjusted under 35 U.S.C. 154(b) by 0 days.

(21) Appl. No.: 13/704,830

(22) PCT Filed: Jun. 15, 2010

(86) PCT No.: PCT/SG2010/000226
§ 371 (c)(1),
(2), (4) Date: Dec. 17, 2012

(87) PCT Pub. No.: WO2011/159250
PCT Pub. Date: Dec. 22, 2011

(65) Prior Publication Data
US 2013/0085364 A1    Apr. 4, 2013

(51) Int. Cl.
*A61B 5/04* (2006.01)
*A61B 5/00* (2006.01)
*A61B 5/0404* (2006.01)
*G06F 19/00* (2011.01)
*A61B 5/0408* (2006.01)

(52) U.S. Cl.
CPC ............ *A61B 5/0006* (2013.01); *A61B 5/0022* (2013.01); *A61B 5/0404* (2013.01); *G06F 19/3418* (2013.01); *A61B 5/0408* (2013.01)

(58) Field of Classification Search
None
See application file for complete search history.

(56) References Cited

U.S. PATENT DOCUMENTS

| | | | |
|---|---|---|---|
| 7,511,623 B2 | 3/2009 | Tice | |
| 2002/0120201 A1 | 8/2002 | Chio et al. | |
| 2002/0147850 A1* | 10/2002 | Richards et al. | 709/248 |
| 2004/0034284 A1 | 2/2004 | Aversano et al. | |
| 2005/0120201 A1 | 6/2005 | Benaloh et al. | |
| 2012/0163663 A1* | 6/2012 | Masoud et al. | 382/103 |

FOREIGN PATENT DOCUMENTS

| | | |
|---|---|---|
| EP | 1383423 | 1/2004 |
| EP | 1815784 | 8/2007 |
| WO | WO 0208765 | 1/2002 |
| WO | WO 2007033166 | 3/2007 |

* cited by examiner

*Primary Examiner* — Brian T Gedeon
*Assistant Examiner* — Ankit Tejani

(57) ABSTRACT

A system for facilitating remote medical diagnosis and consultation of heart disease for a patient, the system comprising: a diagnostic device for performing Electrocardiography on the patient, a network device in communication with the diagnostic device via wired or wireless communication links, a software program pre-installed in the network device, a server located remotely, wherein during operation, the patient activates the diagnostic device which will perform Electrocardiography on the patient, the diagnostic device receives diagnostic data and transmits the diagnostic data to the network device, the software program transmit the diagnostic data to over a network to a server which a physician have access to, and based on the diagnostic data gathered by the server and some additional medical data, the physician can review the patient's health condition and offer an appropriate feedback and diagnosis for the patient.

14 Claims, 9 Drawing Sheets

METHOD AND SYSTEM FOR FACILITATING REMOTE MEDICAL DIAGNOSIS AND CONSULTATION

CROSS REFERENCE TO RELATED APPLICATIONS

This application is a National Phase Application claiming the benefit and priority of International Patent Application number PCT/SG2010/000226, filed Jun. 15, 2010, currently pending, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

Non-limiting exemplary embodiments of the present disclosure relate to a method and system for facilitating remote medical diagnosis and consultation, in particularly in the medical diagnosis and consultation of heart disease.

2. Background

In traditional health care system, medical diagnosis and consultation is conducted face to face between the patients and the doctors in the clinics and hospitals. The traditional health care system requires that a patient visit a clinic or hospital for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Furthermore, the patient's medical records are also kept for record purpose in the clinics and hospitals.

The health care industry is undergoing an evolution by integrating Information Technology (IT). One such application of the Information Technology facilitates remote medical diagnosis and consultation.

A technology-based health care system that fully integrates the technical and social aspects of patient care and therapy should be able to flawlessly connect the client with care providers irrespective of separation distance or location of the participants. While clinicians will continue to treat patients in accordance with accepted modem medical practice, developments in communications technology are making it ever more possible to provide a seamless system of remote patient diagnostics, care and medical services in a time and place independent manner.

There exist many systems and methods with the objective of facilitating remote medical diagnosis and consultation. Some examples of such systems and methods are described as follows.

International Application No. PCT/US2003/038603 discloses a method for remote medical consulting which includes collecting diagnostic data using at least one wearable device contoured to at least a portion of a person's hand, transmitting the diagnostic data to a remote location, transmitting audio data and video images of the patient to the remote location, and communicating diagnosis and/or treatment information to the patient based at least in part on the diagnostic data. The treatment information may include a prescription electronically transmitted to the patient or a pharmacy. The method includes billing of the patient via credit or debit card, bank account, or a third party, such as an insurance company. The diagnostic data as well as the audio and video data may be transmitted wirelessly via cellular or satellite communication networks and/or using a wide area computer network such as the internet.

U.S. patent application Ser. No. 10/801,709 disclose a system for remote consultation via a remote mobile communication apparatus having a unit of medical equipment, a medical server and a remote medical communication apparatus. A method for remote consultation employs the medical equipment to produce the first medical record and store it into the medical server to the remote mobile communication apparatus via a wireless communication network, browse the first medical record, increase, modifies or varies the medical images or medical text of the first medical report to form a second medical report, and use the mobile communication apparatus to send the second medical report back to the medical server via the wireless communication network. The remote consultation can be reached.

U.S. Pat. No. 6,816,603 discloses a method and apparatus for remote medical monitoring incorporating video processing and system of motor tasks. Video image data is received in the form of a sequence of images representative of a subject performing one or more predetermined tasks within a new environment. A plurality of silhouettes is generated from the video image data and combined to provide a motion portrait. Motion characteristics are then calculated based on the motion portrait and may be compared with normal or previous motion characteristics as part of diagnostic analysis.

U.S. Pat. No. 6,418,346 discloses an apparatus and method for remote therapy and diagnosis in medical devices via interface systems. A system for transferring data into and out of medical devices wherein a personal data manager (PDM) is used in a web-based network is disclosed. The PDM cooperates with a programmer to enhance remote monitoring of implanted medical devices on a chronic basis to deliver clinical therapy in real time. The PDM is hand-holdable and mobile and expands the reach of the programmer by storing and forwarding data from the programmer to web-based network constituting a medical environment. The PDM is also implemented to store and forward information to PCs and similar peripheral equipment. In a specialized application, the PDM is configured to exchange data with the unregulated operational/functional segments of the IMD.

However, the above described examples of systems and methods do not cover remote medical diagnosis and consultation of heart disease.

It is an object of the present invention to provide a method and system to facilitate remote medical diagnosis and consultation of heart disease.

It is another object of the present invention to provide a method and system for patients to have more control and awareness over their medical records.

It is yet another object of the present invention to provide a method and system that can save traveling time for patients as a result of remote medical diagnosis and consultation of any heart disease.

It is a further object of the present invention to provide a method and system whereby the doctor has access to more accurate and longer medical records of the patients.

It is another further object of the present invention to provide a method and system to enable pharmacist to refill prescription and administrator to bill payment to the patients.

Other objects and advantages of the present invention will become apparent from the following description, taken in connection with the accompanying drawings, wherein, by way of illustration and example, an embodiment of the present invention is disclosed.

SUMMARY OF THE NON-LIMITING EXEMPLARY EMBODIMENTS OF DISCLOSURE

In accordance with a first aspect of the present invention, there is provided a system for facilitating remote medical diagnosis and consultation of heart disease for a patient, the system comprising: a diagnostic device for performing Electrocardiography on the patient, a network device in communication with the diagnostic device via wired or wireless communication links, a software program pre-installed in the network device, a server located remotely, wherein during operation, the patient activates the diagnostic device which will perform Electrocardiography on the patient, the diagnostic device receives diagnostic data and transmits the diagnostic data to the network device, the software program transmit the diagnostic data to over a network to a server which a physician have access to, and based on the diagnostic data gathered by the server and some additional medical data, the physician can review the patient's health condition and offer an appropriate feedback and diagnosis for the patient.

In accordance with a second aspect of the present invention, there is provided a method for facilitating remote medical diagnosis and consultation of heart disease for a patient, the method comprising steps to conduct Electrocardiography on the patient, the steps comprising: providing a diagnostic device having leads, providing a network device having a pre-installed Electrocardiography recording program, the diagnostic device in communication with the network device, checking if the leads are pasted on the patient, activating the Electrocardiography operation on the patient if all the leads are pasted on the patient, gathering diagnostic data by the Electrocardiography recording program, completing the Electrocardiography operation when all the diagnostic data is gathered by the Electrocardiography recording program.

In accordance with a third aspect of the present invention, there is provided a method for facilitating remote medical diagnosis and consultation of heart disease for a patient, the method comprising steps to conduct the Electrocardiography on the patient, the steps comprising: providing a diagnostic device having leads, providing a network device having a pre-installed Electrocardiography recording program, the diagnostic device in communication with the network device, checking if all the leads are pasted on the patient, activating a reminder signal if not all the leads are pasted on the patient, choosing a single lead mode, activating the Electrocardiography operation on the patient if the single lead is pasted on the body, gathering diagnostic data by the Electrocardiography recording program, completing the Electrocardiography operation when all the diagnostic data is gathered by the Electrocardiography recording program.

In accordance with a fourth aspect of the present invention, there is provided a method for facilitating remote medical diagnosis and consultation of heart disease for a patient, the method comprising steps to conduct Electrocardiography on the patient, the steps comprising: providing a diagnostic device having leads, providing a network device having a pre-installed Electrocardiography recording program, the diagnostic device in communication with the network device, checking if the leads are pasted on the patient, activating a reminder signal if not all the leads are pasted on the patient, choosing a multiple lead mode, rechecking if all the leads are pasted on the patient, activating the Electrocardiography operation on the patient if all the leads is pasted on the body, gathering diagnostic data by the Electrocardiography program, completing the Electrocardiography operation when all the diagnostic data is gathered by the Electrocardiography recording program.

In accordance with a fifth aspect of the present invention, there is provided a method for facilitating remote medical diagnosis and consultation of heart disease for a patient, the method comprising steps of an Electrocardiography operation on a body of the patient, the step comprising: providing a diagnostic device having leads, providing a network device having a pre-installed Electrocardiography recording program, the diagnostic device in communication with the network device, displaying a status diagram on the network device illustrating on the status diagram whether the leads have been pasted on the body of the patient, providing indication to the patient if a lead is to be pasted on a right leg of the patient, pasting the lead on the right leg of the patient, providing indication by the status diagram for the lead to be pasted on the left leg, pasting the lead on the left leg of the patient, sending the diagnostic data by a MCU from the diagnostic device to the network device, gathering the diagnostic data by the Electrocardiography recording program, completing the Electrocardiography operation when all the diagnostic data is gathered by the Electrocardiography recording program, stopping the blinking of left leg indicator, analysing the diagnostic data for sampling, completing the analysing of the diagnostic data.

In accordance with a sixth aspect of the present invention, there is provided for facilitating remote medical diagnosis and consultation of heart disease for a patient, the method comprising steps of an Electrocardiography operation on a body of the patient, the step comprising: providing a diagnostic device having leads, providing a network device having a pre-installed Electrocardiography recording program, the diagnostic device in communication with the network device, displaying a status diagram on the network device illustrating on the status diagram whether the leads have been pasted on the body of the patient, providing indication to the patient if a lead is to be pasted on a right leg of the patient, pasting the lead on the right leg of the patient, providing indication by the status diagram for the lead to the pasted on the left arm, pasting the lead on the left arm of the patient, sending the diagnostic data by a MCU from the diagnostic device to the network device, gathering the diagnostic data by the Electrocardiography recording program, completing the Electrocardiography operation when all the diagnostic data is gathered by the Electrocardiography recording program, stopping the blinking of left arm indicator, analysing the diagnostic data for sampling, completing the analysing of the diagnostic data.

In accordance with a seventh aspect of the present invention, there is provided a method for facilitating remote medical diagnosis and consultation of heart disease for a patient, the method comprising steps of an Electrocardiography operation on a body of the patient, the step comprising: providing a diagnostic device having leads, providing a network device having a pre-installed Electrocardiography recording program, the diagnostic device in communication with the network device, displaying a status diagram on the network device illustrating on the status diagram whether the leads have been pasted on the body of the patient, providing indication to the patient if a lead is to be pasted on a right leg of the patient, pasting the lead on the right leg of the patient, providing indication by the status diagram for the lead to the pasted on the right arm, pasting the lead on the right arm of the patient, sending the diagnostic data by a MCU from the diagnostic device to the network device, gathering the diagnostic data by the Electrocardiography recording program, completing the Electrocardiography operation when all the diagnostic data is gathered by the Electrocardiography recording program, stopping the blinking of right arm indicator, analysing the diagnostic data for sampling, completing the analysing of the diagnostic data.

In accordance with a eighth aspect of the present invention, there is provided a method for facilitating remote medical diagnosis and consultation of heart disease for a patient, the method comprising steps of an Electrocardiography operation on a body of the patient, the step comprising: providing a diagnostic device having leads, providing a network device having a pre-installed Electrocardiography recording program, the diagnostic device in communication with the network device, displaying a status diagram on the network device illustrating on the status diagram whether the leads have been pasted on the body of the patient, providing indication to the patient if a lead is to be pasted on a right leg of the patient, pasting the lead on the right leg of the patient, providing indication by the status diagram for the lead to the pasted on the chest, pasting the lead on the chest of the patient, sending the diagnostic data by a MCU from the diagnostic device to the network device, gathering the diagnostic data by the Electrocardiography recording program, completing the Electrocardiography operation when all the diagnostic data is gathered by the Electrocardiography recording program, stopping the blinking of chest indicator, analysing the diagnostic data for sampling, completing the analysing of the diagnostic data.

In accordance with a ninth aspect of the present invention, there is provided a method for facilitating remote medical diagnosis and consultation of heart disease for a patient, the method comprising a plurality of working protocols between the patient and a physician, the method comprising: providing a diagnostic device according to claim 1, authorising the physician to append one or more health data, the health data comprising an appropriate feedback and diagnosis for the patient from the physician, analysing the diagnostic data by the physician, offering an appropriate feedback and diagnosis for the patient, transmitting a health data to the patent from the server to the network device, the health data containing the appropriate feedback and diagnosis, saving the health data accordingly to the patient's profile in a depository within the server, displaying the health data on a display screen on the network device, having an option to request for more feedback regarding health condition of the patient.

In accordance with a tenth aspect of the present invention, there is provided a method for facilitating remote medical diagnosis and consultation of heart disease for a patient, the method comprising steps to provide feedback based on an analysis of a health data of the patient, the step comprising: providing a diagnostic device according to claim 1 receiving health data by the network device, the health data comprising the appropriate feedback and diagnosis for the patient from the physician, analysing the health data with an analysis tool program pre-installed in the network device, checking if the health data exceed a certain limit, when the health data do not exceed the limit, the analysis tool program produces a feedback report informing the patient that the health data is normal and that the patient health condition is healthy, when the health data exceed the limit, the analysis tool program produces a feedback report informing the patient that the health data is not normal and necessary actions and steps have to be taken to improve the patient health condition, having an option whether to go for a medical check-up or an investigation or not at all, when choosing to go for medical check-up, the patient will be given a necessary remedy to his health condition. when choosing to go for investigation, the health data is sent to a technician for analyse and investigation, and a completed analysis result is sent back to the patient, if the health data require further analysis and investigation, the health data is be sent to a physician for a further analysis and investigation, and a completed analysis result will then be sent back to the patient, the completed analysis results containing advice from the physician to go for a medical check-up, having an option whether to go for a medical check-up or not, when choosing to go for medical check-up, the patient will be given a necessary remedy to his health condition.

BRIEF DESCRIPTION OF THE DRAWINGS

By way of example/illustration only, an embodiment of the invention is described more fully hereinafter with reference to the accompanying drawings, in which:—

DETAILED DESCRIPTION OF NON-LIMITING EXEMPLARY EMBODIMENTS OF THE DISCLOSURE

Figure 1:
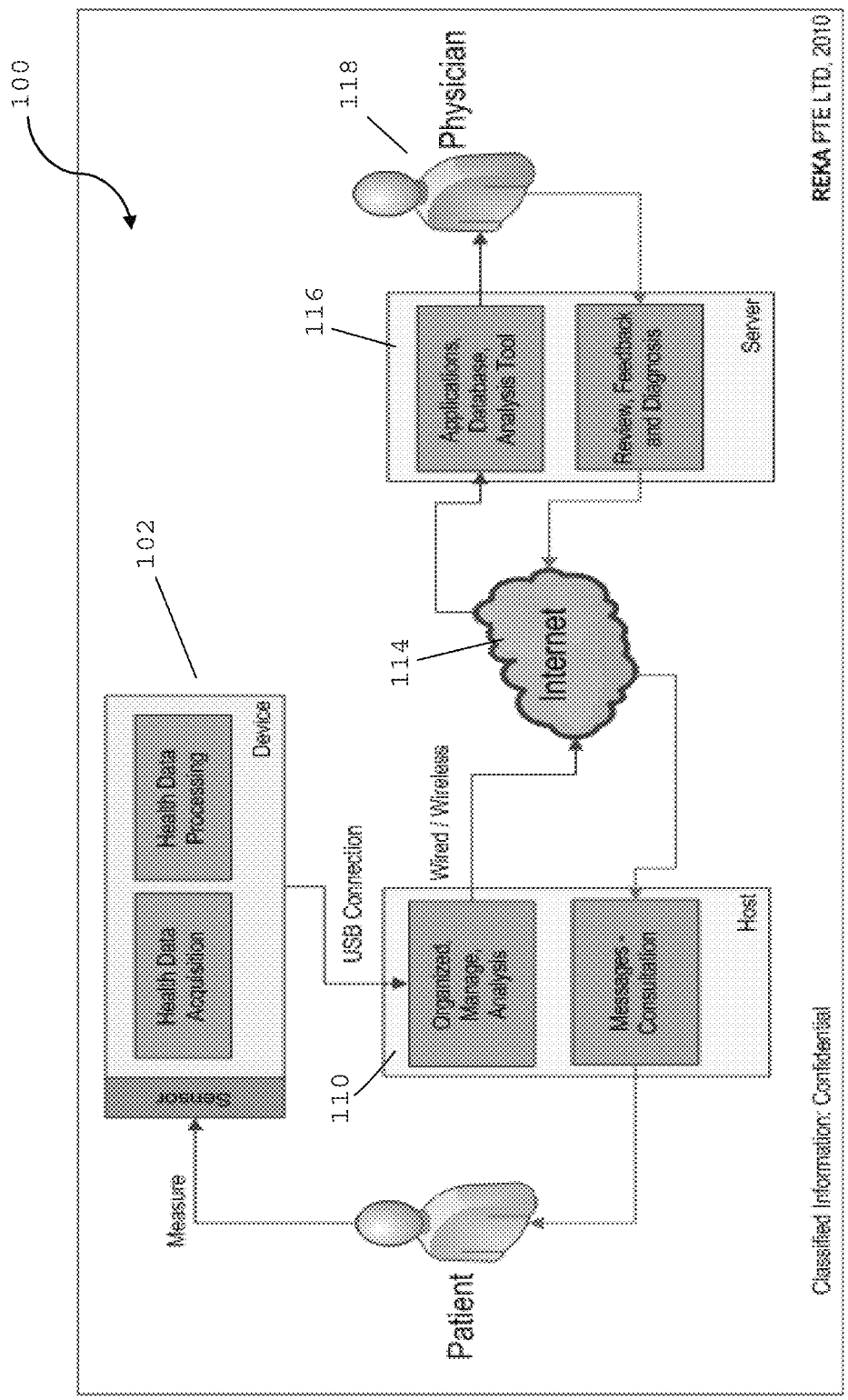
FIG. 1 is a graphical representation illustrates a system for facilitating remote medical diagnosis and consultation of heart disease in a preferred embodiment of the present invention.

Referring now to FIG. 1, a graphical representation illustrates a system 100 for facilitating remote medical diagnosis and consultation of heart disease in a preferred embodiment of the present invention.

Figure 2:
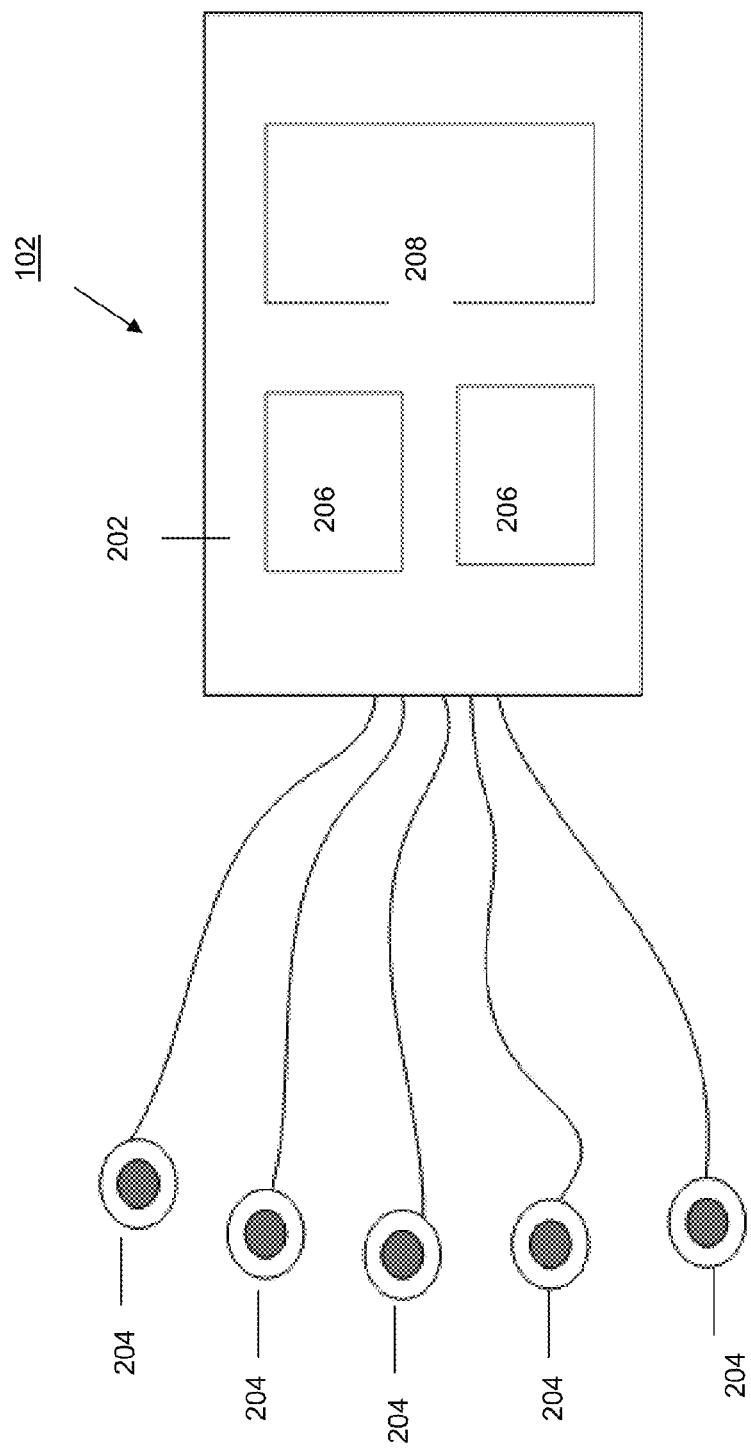
FIG. 2 shows a diagnostic device includes sensors which are electrically connected to an interface unit and secured to the interface unit in a preferred embodiment of the present invention.
Figure 3:
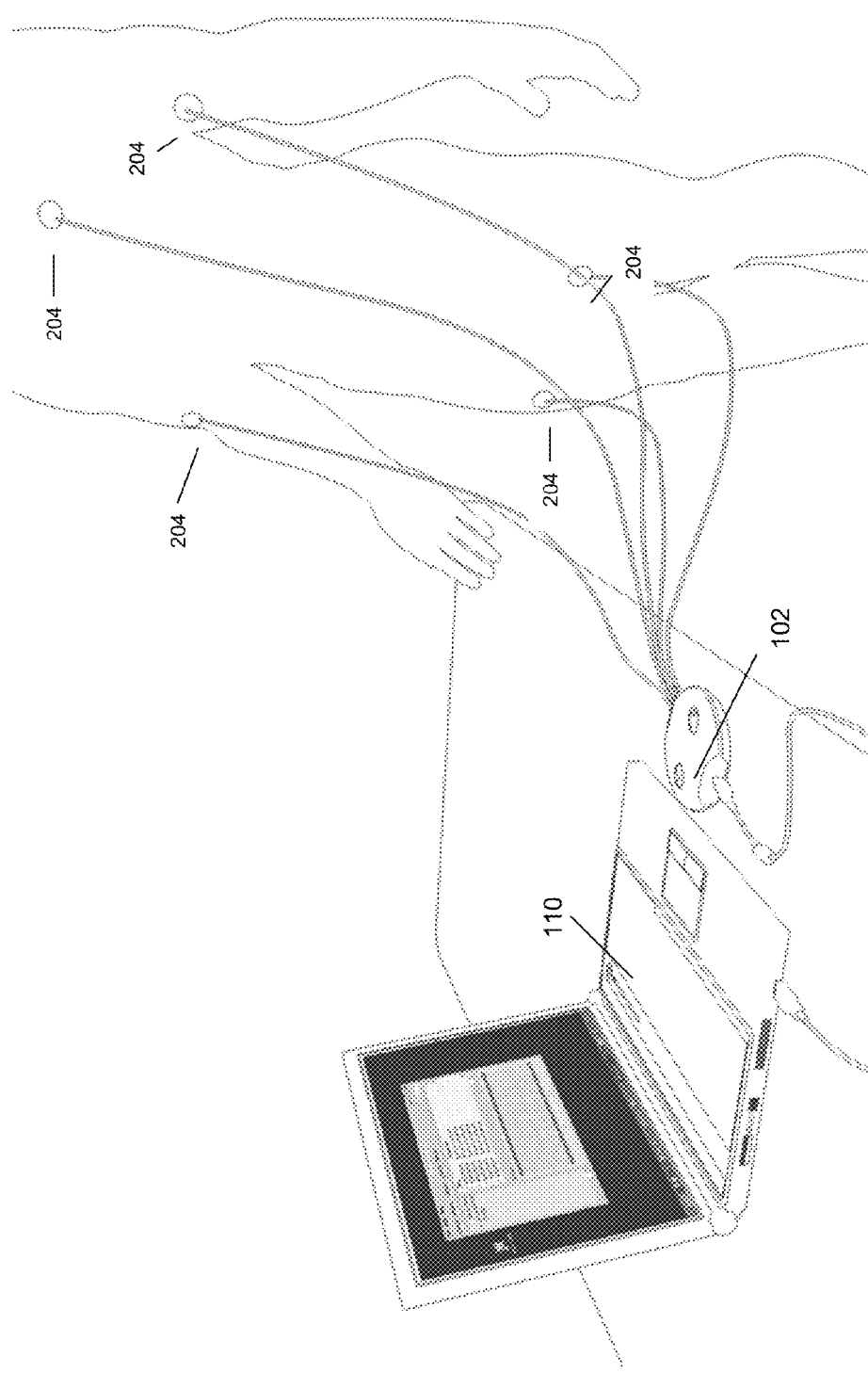
FIG. 3 shows the patient placing the sensors on certain parts of the body when in use.
Figure 4:
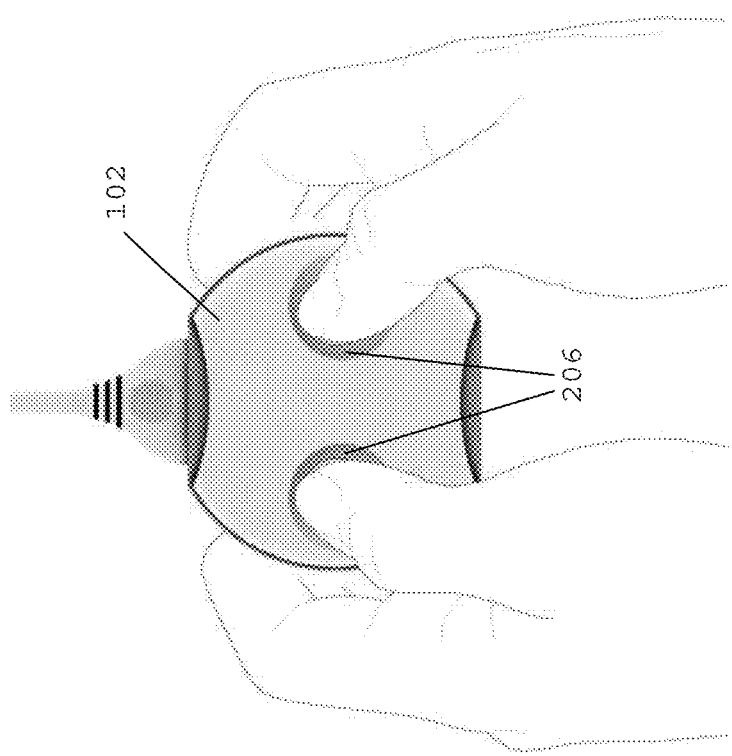
FIG. 4 shows the patient placing his fingers on the sensors attached on the diagnostic device.

In the preferred embodiment, referring to FIG. 2 in conjunction with FIG. 3 and FIG. 4, diagnostic device 102 includes sensors in the form of electrodes which are electrically connected 204 to an interface unit 202 and secured to the interface unit 202. The interface unit 202 may contain a compact, consolidated circuit board unifying various processing circuitry to condition signals received from the sensors for local display 208 of corresponding information.

When in use, the patient places the sensors 204 on certain parts of the body as shown in FIG. 3. Alternatively, the patient may place his fingers on the sensors 206 attached on the diagnostic device 102 as shown in FIG. 4. A detecting software program pre-installed within the network device 110, detect the diagnostic data from the sensors 204, 206. If the diagnostic data falls within a range of health parameters, the detecting software program will permit the operation of the Electrocardiography (ECG) recording program (which will be described more in detail later).

Thereafter, referring to FIG. 1, the patient activates the diagnostic device 102 which will perform Electrocardiography (ECG) on the body. As will be appreciate by those of ordinarily skilled in the art, Electrocardiography is a transthoracic interpretation of the electrical activity of the heart over time captured and externally recorded by the sensors. It is a non-invasive recording produced by the diagnostic unit 102. The diagnostic unit 102 is also commonly known as electrocardiographic device.

The ECG works by detecting and amplifying the tiny electrical changes on the skin that are caused when the heart muscle "depolarises" during each heartbeat. At rest, each heart muscle cell has a charge across its outer wall, or cell membrane. Reducing this charge towards zero is called depolarisation, which activates the mechanisms in the cell that cause it to contract. During each heartbeat a healthy heart will have an orderly progression of a wave of depolarisation that is triggered by the cells in the sinoatrial node, spreads out through the atrium, passes through "intrinsic conduction pathways" and then spreads all over the ventricles. This is detected as tiny rises and falls in the voltage between two sensors placed either side of the heart which is displayed as a wavy line either on a screen or on paper. This display indicates the overall rhythm of the heart and weaknesses in different parts of the heart muscle.

ECG is the best way to measure and diagnose abnormal rhythms of the heart, particularly abnormal rhythms caused by damage to the conductive tissue that carries electrical signals, or abnormal rhythms caused by electrolyte imbalances. In a myocardial infarction (MI), the ECG can identify if the heart muscle has been damaged in specific areas, though not all areas of the heart are covered. The ECG cannot reliably measure the pumping ability of the heart, for which ultrasound-based (echocardiography) or nuclear medicine tests are used. It is possible to be dead with a normal ECG signal (a condition known as pulseless electrical activity).

After the diagnostic device 102 performs the ECG on the patient, the diagnostic device 102 receives diagnostic data and transmits the diagnostic data to a network device 110 (also known as "Host") which is in communication with the diagnostic device 102 via wired or wireless communication links. A USB connection is shown in FIG. 1 as an example of a wired communication link. The diagnostic device 102 is compatible with many types of network device 110 without any requirement to change any hardware within the diagnostic device 102. The network device 110 may be a desktop computer, laptop computer, smart phone, mobile phone, handheld computer or personal digital assistance (PDA). The network device 110 may operate under different operating system, such as Microsoft Windows, Apple OSX and Linux. In addition, the network device 110 may include application software program to operate it.

A software program is pre-installed in the network device 110. The software program enables the patient to control the operation of the diagnostic device 102 and also to receive the diagnostic data captured by the diagnostic device 102 after the ECG is performed. More specifically, the software program organizes the diagnostic data in a specific format. For instance, the diagnostic data may be tabulated according to the date and timing which the ECG is performed.

In addition, the software program also summarizes and manages the diagnostic data and conduct analysis on the diagnostic data. In a preferred embodiment of the present invention, the software program is able to analyse heart rate based on the diagnostic data from the diagnostic device. The heart rate analysis makes use of the algorithms performing the following steps:
 a. The algorithm may refer to Pan-Tomkins method to convert ECG to a square wave form.
 b. The said square wave form is determined based on the change of vector direction of ECG complex.
 c. The intervals of these square waves are stored in a temporary memory medium.
 d. These intervals data are analysed and subsequently grouped.
 e. The longest interval group is then identified.
 f. The rising edge of longest interval to next rising edge of longest interval will be displayed as heart rate.

The software program also enables the diagnostic data to be transmitted from the network device 110 over local and/or wide area network or internet 114 to a remotely located server 116 using any of a number of available transmission modes, such as telephone or cable modem, digital subscriber loop (DSL), satellite, etc.

The server 116 contains a valuable resource for medical practitioner (also known as physician) 118 for diagnosis and treatment based on the patient's diagnostic data gathered. The sever 116 may be of a number of commercially available or proprietary system used to assist in diagnosing various illness and providing recommended treatment regimens.

In the preferred embodiment of the present invention, the server 116 contains pre-installed software programs, such as application software programs, database and analysis tool program.

The application software programs are designed to help the user to perform singular or multiple specific tasks. Some examples of application software programs include health data file manager, ECG graph viewer and health data trend plotter (in graph format).

The database consists of software-based "containers" that are structured to collect and store information so that users can retrieve, add, update or remove such information in an automatic fashion. Database programs are designed for users so that they can add or delete any information needed. The structure of a database is tabular, consisting of rows and columns of information.

Analysis tool are conceptual model which captures an abstraction of a situation that can often be encountered in modelling. An analysis pattern can be represented as "a group of related, generic objects (meta-classes) with stereotypical attributes (data definitions), behaviours (method signatures), and expected interactions defined in a domain-neutral manner.

A physician 118 having access to the server 116 can have a good knowledge on the patient's health condition. Based on the diagnostic data gathered by the server 116 and some additional medical data, the physician 118 can review the patient's health condition and offer an appropriate feedback and diagnosis for the patient.

Due to the confidentiality of the diagnostic data stored in the database within the server 116 and also the appended health data stored according to the patient's profile in the depository within the server 116 (which will be further described in FIG. 8), there exist security measures to protect against any unauthorised access to the server 116. In a preferred embodiment of the present invention, the diagnostic device 102 acts as a security hardware lock to gain access to the server 116. More specifically, the diagnostic device 102 is flashed with a unique identifier which may be a serial number. The network device 110 conducts an authenticity test on the serial number of the diagnostic device 102. If the authenticity test is positive, the network device 110 is granted communication access to the server 116 and thus permits diagnostic data to be transmitted from the network device 110 to the server 116 and also permits health data to be transmitted from the server 116 to the network device 110.

In another embodiment, the hardware/software associate with the server 116 performs various tasks utilizing one or more programmed microprocessors and related temporary and permanent computer readable storage media. Computer readable storage media may include various programs, modules, databases, and the like to perform consultation routing and scheduling functions, billing and payment functions, and patient medical history storage and retrieval functions. A local knowledge base may also be provided for use by physician to provide diagnosis and treatment advice. The server may also be used to control bio-data adjustment software/hardware, which is used to provide the physician with flexibility in calibrating or correcting sensor output from diagnostic unit. This provides one layer of back-up or redundancy that is incorporated into the consultation system. Routing/scheduling module of the server may perform a triage function of routing consultation requests by urgency with emergency requests routed to an appropriate emergency response centre and scheduling routine or follow-up consultations via one or more virtual offices.

Feedback and diagnosis for the patient offered by the physician 118 is transmitted from the server 116 over local and/or wide area network or internet 114 back to the network device 110. The health data containing the feedback and diagnosis by the physician 118 is displayed to the patient on a display screen on the network device 110. The health data enables the patient to understand his health condition better and also to be aware of the physician's instructions regarding the necessary steps to take to improve his health condition.

Figure 5:
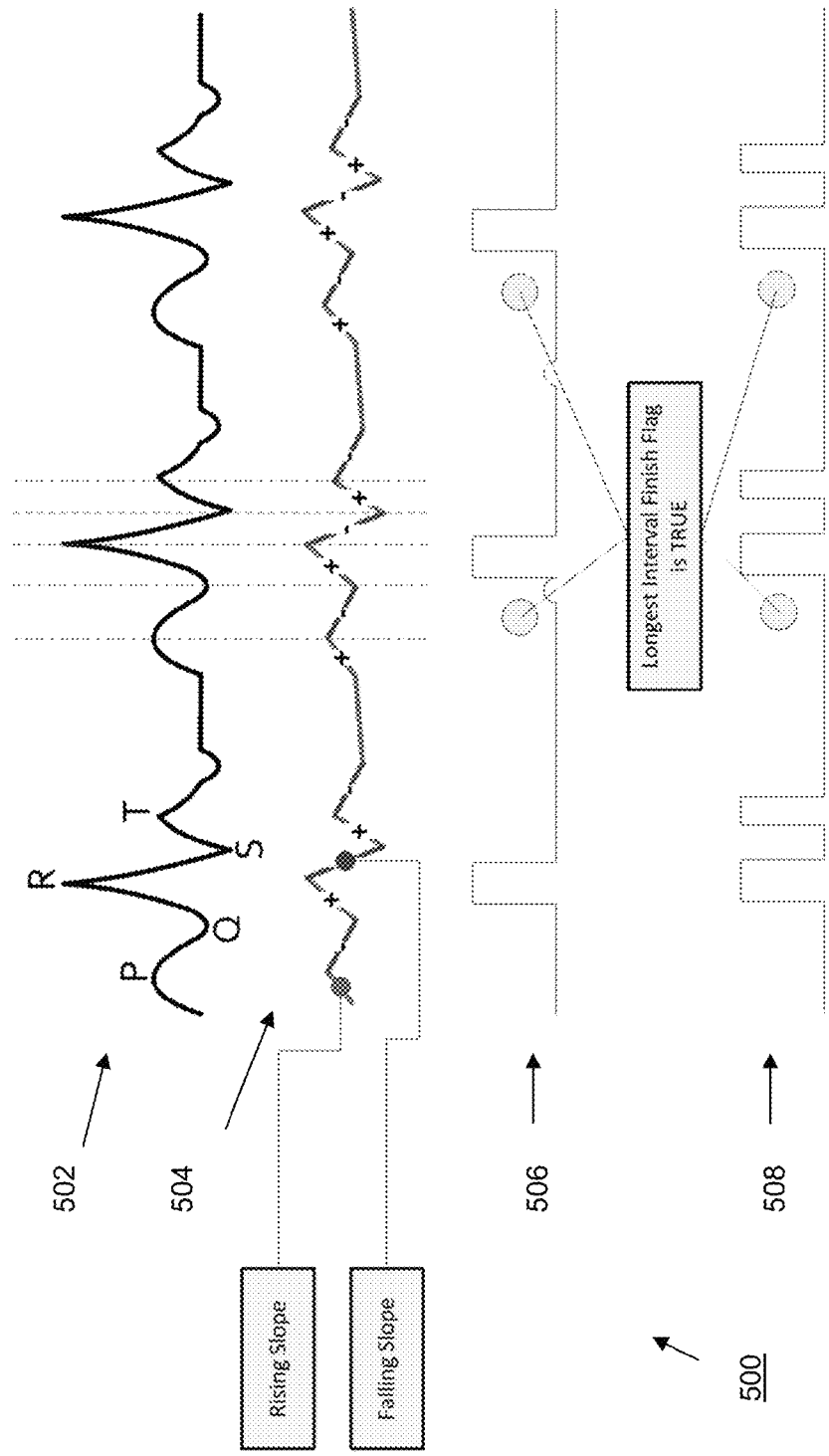
FIG. 5 shows the different representation of the wave forms of the ECG operation performed on the patient's body in a preferred embodiment of the present invention.

FIG. 5 shows the different representation of the wave forms 500 of the ECG operation performed on the patient's body in a preferred embodiment of the present invention.

502 is the actual wave form being displayed on the display screen on the network device. As shown, the wave form 502 comprises of peaks P, R, T and valleys Q, S. PQRST is considered to be one cycle of the wave form 502.

504 is the algorithmic representative of the actual wave form 502. As shown, the algorithmic representative 504 comprises of positive (+) signs and negative (−) signs which correspond to the represent rising slope and falling slope of the actual wave form 502 respectively.

506 is the Pan-Tomkins representative of the actual wave form 502 in an ideal case. Ideal case is "R" peak in the ECG complex is substantially bigger than "T" peak. The algorithm can differentiate the "R" peak and "T" peak. As shown, the wave form 502 is converting by an algorithm, for example Pan-Tomkins method, to a square wave form. The Pan-Tomkins representative comprises of a square wave which correspond to the peak "R" of the actual wave form 502. The longest interval is the distance between the two consecutive square waves corresponding to the peak "R". The rising edge of longest interval to next rising edge of longest interval will be displayed as heart rate of the patient.

508 is the Pan-Tomkins representative of the actual wave form 502 in a "Big T" case. "Big T" case is "R" peak amplitude in the ECG complex is similar to "T" peak amplitude. The algorithm cannot differentiate the "R" peak and "T" peak owing to their amplitude are similar. As shown, the wave form 502 is converting by an algorithm, for example Pan-Tomkins method, to a square wave form. The Pan-Tomkins representative comprises of a square wave which correspond to the peak "R" and "T" of the actual wave form 502. The longest interval is the distance between the two consecutive square waves corresponding to the peak "T" and "R". The rising edge of longest interval to next rising edge of longest interval will be displayed as heart rate of the patient.

In order for different representation of the wave forms of the ECG operation performed on the patient's body to be displayed, the network device is pre-installed with an algorithms which perform the follow function:

g. The algorithm is to detect the ECG complex difference from cycle to cycle.
h. The algorithm can accept an input value of difference, a.k.a., tolerance from a user of the device.
i. The algorithm first detects the highest amplitude of ECG data. The highest amplitude is marked as 'R'
j. The said algorithm then detects vector differential if it is positive or negative.
k. By referring to ending point of longest interval, the peaks and valleys of ECG complex is identified. The said peaks and valleys of the ECG complex are PQRST values in ECG. (Refer to flow chart)
l. The values of P, Q, R, S and T intervals with reference to said ending point of longest interval are stored in memory.
m. The algorithm compares the P, Q, R, S and T intervals of one cycle of ECG to the next cycle of ECG.

When the P, Q, R, S and T intervals from cycle to cycle found difference greater than the said tolerance values, the device will send a message of abnormality to the user of the network device.

Figure 6:
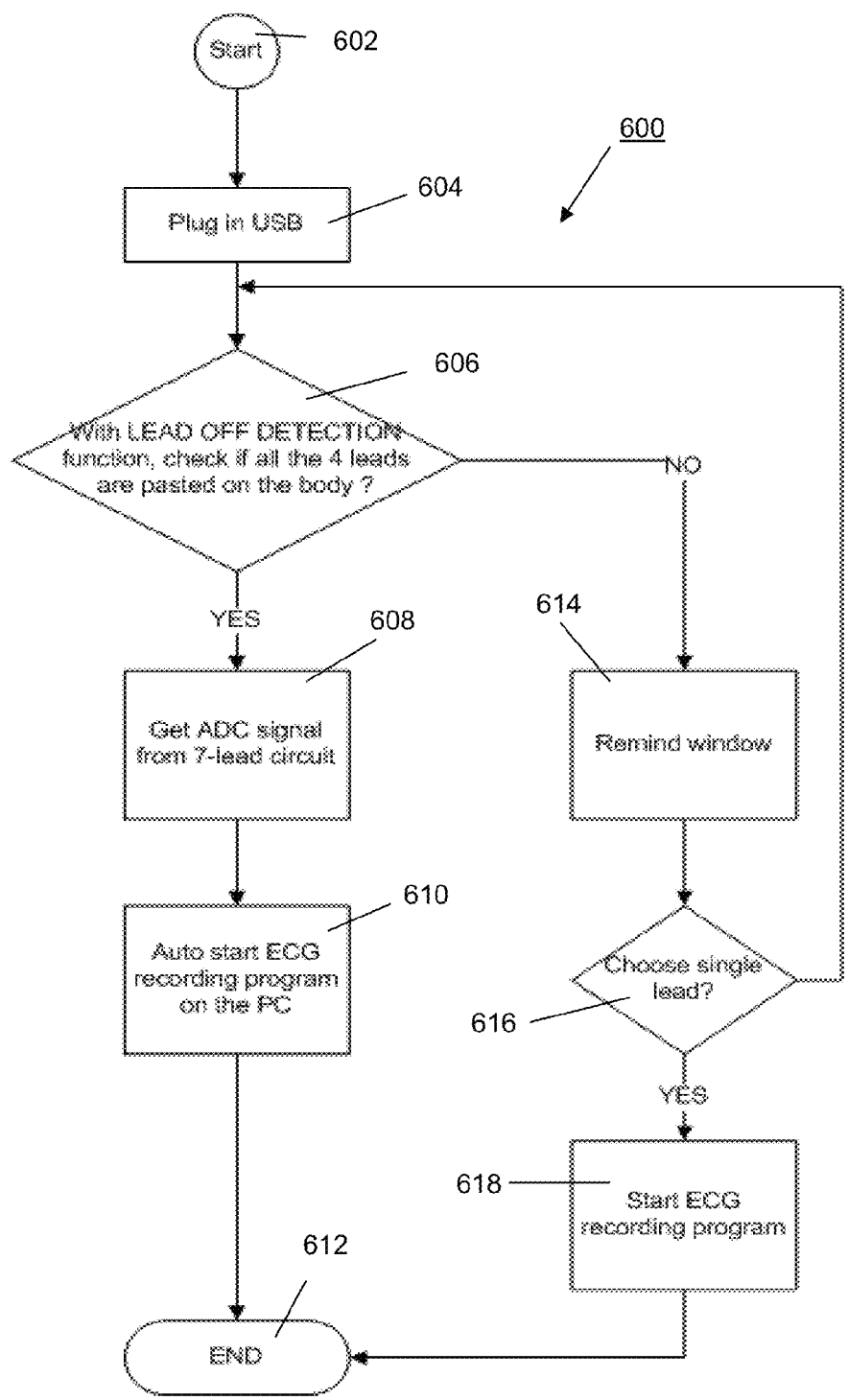
FIG. 6 is the flow chart showing the steps to take to conduct the ECG on the patient in a preferred embodiment of the present invention.

FIG. 6 is the flow chart 600 showing the steps to take to conduct the ECG on the patient in a preferred embodiment of the present invention.

Processing commences in step 602.

The patient first plug the USB connection onto the diagnostic device 102 and the network device 110 such that the diagnostic device 102 is in communication with the network device 110 in step 604 in a preferred embodiment of the present invention. The USB may use a personal health device class (PHDC) to communicate with the Host. In other embodiments, the USB connection can be replaced by other wired or wireless communication links.

In the preferred embodiment of the present invention, the diagnostic device has a "Lead Off Detection" function which enables the patient to check if all the 4 leads are pasted on the body in step 606. The leads refer to the sensors with wire connection. It is submitted that the number of leads is not restricted to 4 and the number of leads depends on different applications.

If all the leads are pasted on the body, the 7-lead circuit preinstalled within the diagnostic device will produce an analogue-to-digital conversion (ADC) signal which will activate the ECG operation on the patient's body in step 608 in a preferred embodiment of the present invention.

In step 610, the ECG recording program preinstalled in the network device 102 starts its operation automatically after the ECG operation is activated in a preferred embodiment of the present invention. Diagnostic data from the diagnostic device 102 performing the ECG is gathered by the ECG recording program.

The processing end in step 612 when the ECG operation is completed and all the diagnostic data is gathered by the ECG recording program preinstalled in the network device 102.

In situation where not all the leads are pasted on the body, a reminder signal (also known as reminder window) is activated on the diagnostic device in step 614 in a preferred embodiment of the present invention.

When the reminder signal is activated, the patient may choose a single lead mode or multiple lead modes in step 616 in a preferred embodiment of the present invention. It is achieved by having a switching circuit build in within the diagnostic device 102. The switching circuit enable the diagnostic device 102 to switch between a single lead mode and a multiple lead mode.

Single lead is used when the patient prefer convenience like during travel, or when patient want a quick measurement. The advantage of single lead mode is the ECG measurement setup is easy and convenient (without wires). Basically, single lead mode provides only measurement for heart rate and regularity of heart rhythm.

Multi lead mode is used when the patient wants to obtain a more accurate and also more diagnostic data during the measurement. The advantage of multi lead mode is that more diagnostic data is captured and less noise is induced by the diagnostic device. Basically, multi lead mode predicts potential failure of certain chamber and blood vanes.

If the patient wants to perform a multi lead ECG measurement, the patient will repeat step 606 again, that is, to re-check if all the 4 leads are pasted on the body in step 606. In this application, the diagnostic device 102 is switched to a multiple lead mode. If the all the 4 leads are pasted on the body, steps 608 to 612 is to be processed.

If the patient wants to perform a single lead ECG measurement, the patient may activate the ECG measurement by pressing his index finger and thumb onto the build in sensors on the diagnostic device. In this application, the diagnostic device 102 is switched to a single lead mode automatically without further manual input from the patient. In step 618, the ECG recording program preinstalled in the network device start its operation automatically after the ECG operation is activated in a preferred embodiment of the present invention. Diagnostic data from the diagnostic device performing the ECG is gathered by the ECG recording program.

The processing end in step 612 when the ECG operation is completed and all the diagnostic data is gathered by the ECG recording program preinstalled in the network device.

Figure 7:
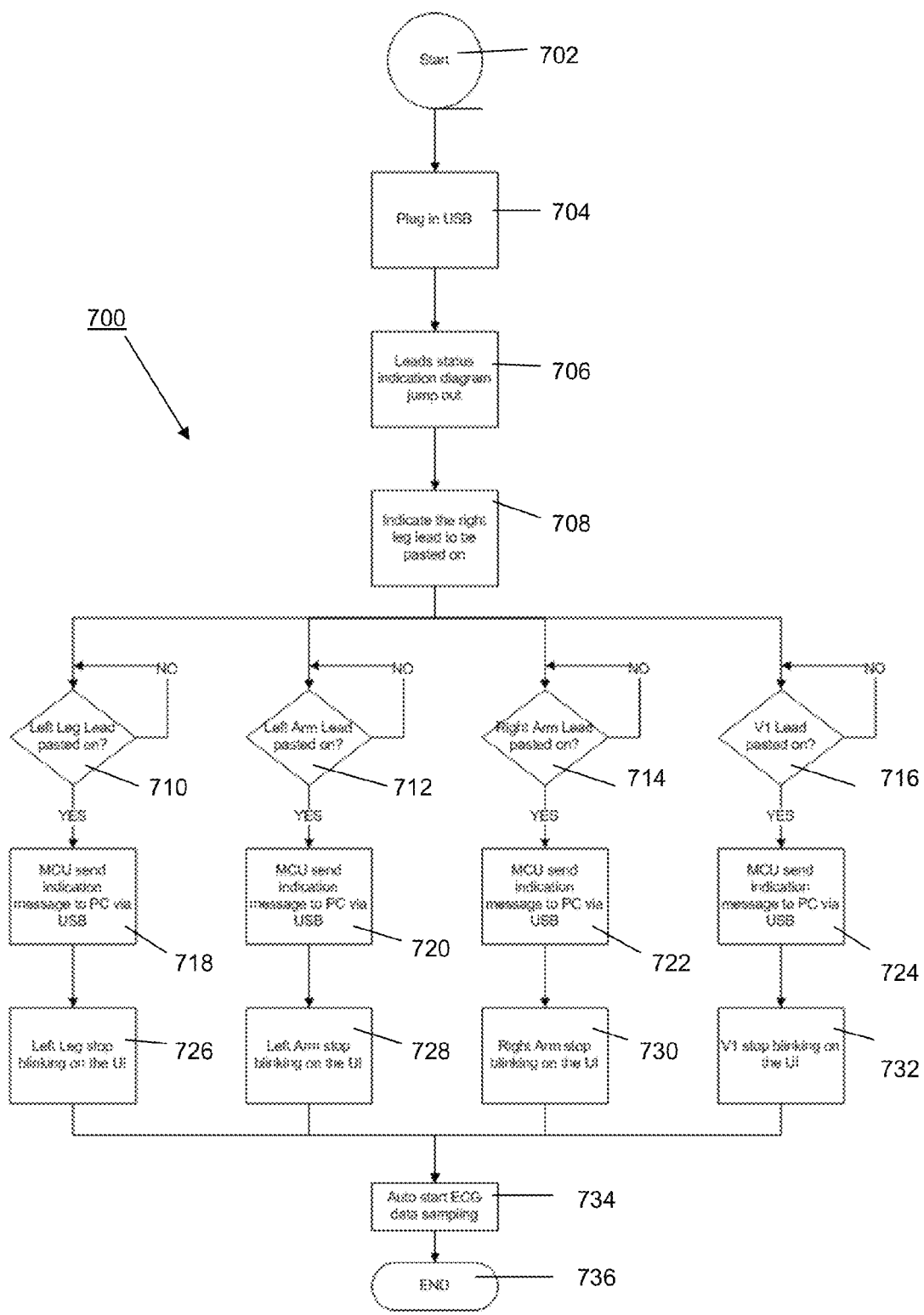
FIG. 7 is the flow chart showing the steps of the ECG operation on the body of the patient in a preferred embodiment of the present invention.

FIG. 7 is the flow chart 700 showing the steps of the ECG operation on the body of the patient in a preferred embodiment of the present invention.

Processing commences in step 702.

The patient first plug the USB connection onto the diagnostic device 102 and the network device 110 such that the diagnostic device 102 is in communication with the network device 110 in step 704 in a preferred embodiment of the present invention. In other embodiments, the USB connection can be replaced by other wired or wireless communication links.

In step 706, a status diagram is displayed on the network device 110 in a preferred embodiment of the present invention. The status diagram is also known more specifically as a leads status indication diagram which illustrates whether the leads have been pasted onto the body of the patient.

In step 708, the leads status indication diagram provides indication to the patient that a lead is to be pasted on the right leg of the patient in a preferred embodiment of the present invention. Since the lead is to be pasted on the right leg of the patient, this lead is also known as right leg lead.

After the lead is pasted on the right leg of the patient, the leads status indication program provides indication for the lead to be pasted on the left leg in step 710 or the lead to be pasted on the left arm in step 712 or the lead to be pasted on the right arm in step 714 or a V1 lead to be pasted on the chest in step 716.

The lead to be pasted on the left leg in step 710 is also known as left leg lead. The lead to be pasted on the left arm in step 712 is also known as left arm lead. The lead to be pasted on the right arm in step 714 is also known as right arm lead. The lead to be pasted on the chest in step 716 is also known as V1 lead.

In these steps 710 to 716, the lead status indication program will remind the patient if the leads have been pasted on the respective body parts, that is, the left leg, the left arm, the right arm and the chest.

Once the leads are pasted on the left leg in step 710, the MCU (Micro Controller Unit) send diagnostic data (sometimes also known as indication message) from the diagnostic device 102 to the network device 110 via the USB connection in step 718 in a preferred embodiment of the present invention. In other embodiments, the USB connection can be replaced by other wired or wireless communication links. The diagnostic data will be gathered by the ECG recording program till the ECG operation is completed. After the ECG operation is completed, the left leg indicator will stop blinking on the UI (User Interface) in step 726.

Once the leads are pasted on the left arm in step 712, the MCU (Micro Controller Unit) send diagnostic data (also known as indication message) from the diagnostic device 102 to the network device 110 via the USB connection in step 720 in a preferred embodiment of the present invention. In other embodiments, the USB connection can be replaced by other wired or wireless communication links. The diagnostic data will be gathered by the ECG recording program till the ECG operation is completed. After the ECG operation is completed, the left arm indicator will stop blinking on the UI (User Interface) in step 728.

Once the leads are pasted on the right arm in step 714, the MCU (Micro Controller Unit) send diagnostic data (also known as indication message) from the diagnostic device 102 to the network device 110 via the USB connection in step 722 in a preferred embodiment of the present invention. In other embodiments, the USB connection can be replaced by other wired or wireless communication links. The diagnostic data will be gathered by the ECG recording program till the ECG operation is completed. After the ECG operation is completed, the right arm indicator will stop blinking on the UI (User Interface) in step 730.

Once the leads are pasted on the chest in step 716, the MCU (Micro Controller Unit) send diagnostic data (also known as indication message) from the diagnostic device 102 to the network device 110 via the USB connection in step 724 in a preferred embodiment of the present invention. In other embodiments, the USB connection can be replaced by other wired or wireless communication links. The diagnostic data will be gathered by the ECG recording program till the ECG operation is completed. After the ECG operation is completed, the V1 indicator will stop blinking on the UI (User Interface) in step 732.

The diagnostic data gathered by the ECG recording program from steps 726, 728, 730 and 732 are analysed for sampling in step 734.

The processing ends in step 736 when the diagnostic data gathered by the ECG recording program have been analysed in step 734.

Figure 8:
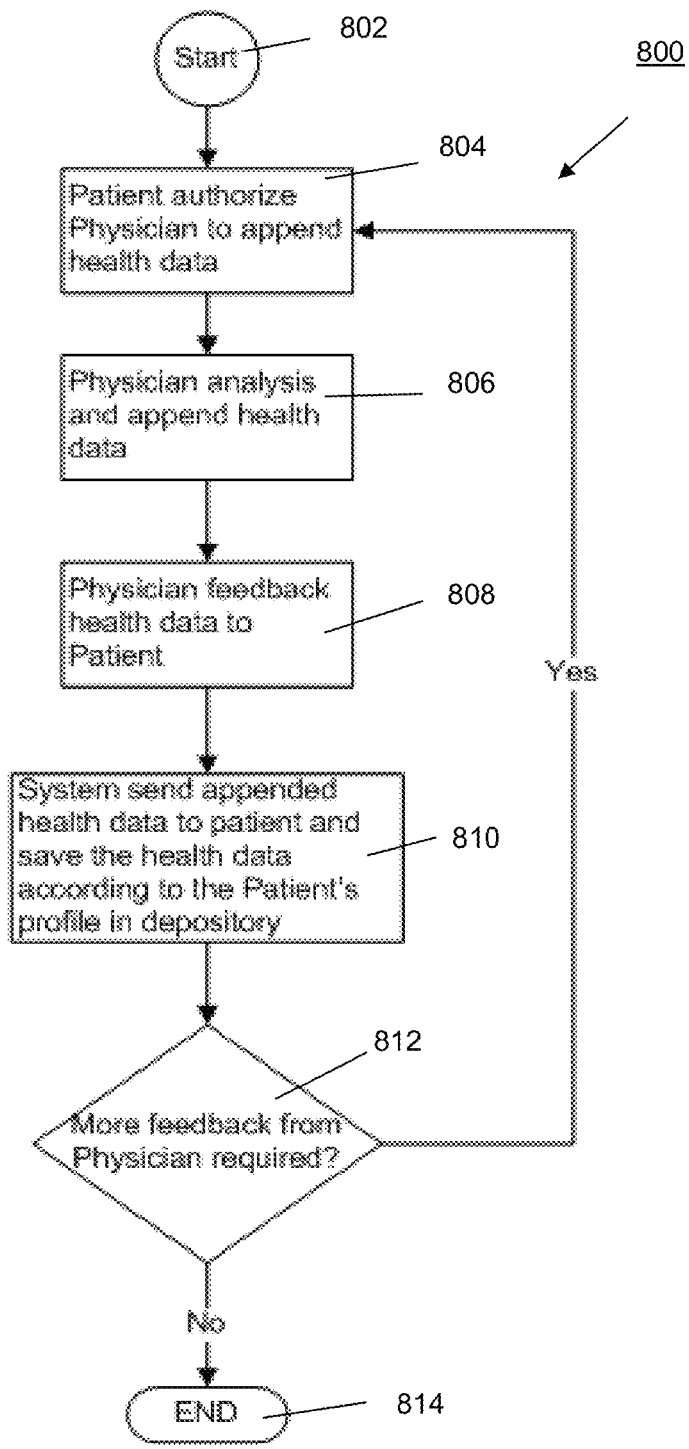
FIG. 8 is the flow chart showing the working protocols between the patient and the physician in a preferred embodiment of the present invention.

FIG. 8 is the flow chart 800 showing the working protocols between the patient and the physician in a preferred embodiment of the present invention.

Processing commences in step 802.

In step 804, the patient authorise the physician to append one or more health data in a preferred embodiment of the present invention. This step is usually taken after the patient has performed the ECG on his body and the diagnostic data has been transmitted to the server which the physician has access to and the patient want to know the health condition of his body and need the physician to review his health condition and offer an appropriate comment, feedback and diagnosis for the patient. Health data contains the appropriate feedback and diagnosis for the patient from the physician. In other embodiment, the comment, feedback and diagnosis offered by the physician may be attached as a meta data to the health data.

In step 806, the physician analyse the diagnostic data gathered by the server in a preferred embodiment of the present invention. Based on the diagnostic data gathered by the server and some additional medical data, the physician 118 can review the patient's health condition and offer an appropriate feedback and diagnosis for the patient. A health data containing the appropriate feedback and diagnosis will be sent by the physician to the patient in step 808.

In step 810, the server transmits or sends the appended health data to the patient and at the same time also save the appended health data accordingly to the patient's profile in the depository within the server, according to a preferred embodiment of the present invention. The appended health data is transmitted from the server 116 over local and/or wide area network or internet 114 back to the network device 110. The health data containing the feedback and diagnosis by the physician is displayed to the patient on a display screen on the network device 110. The health data enables the patient to understand his health condition better and also to be aware of the physician's instructions regarding the necessary steps to take to improve his health condition.

In step 812, the patient have the option to request for more feedback regarding his health condition, based on additional diagnostic data gathered, accordingly to a preferred embodiment of the present invention. If the patient wants to request for more feedback regarding his health condition, steps 804 to 810 are repeated again.

The processing ends in step 814 when the patient do not request for any more feedback regarding his health condition.

Figure 9:
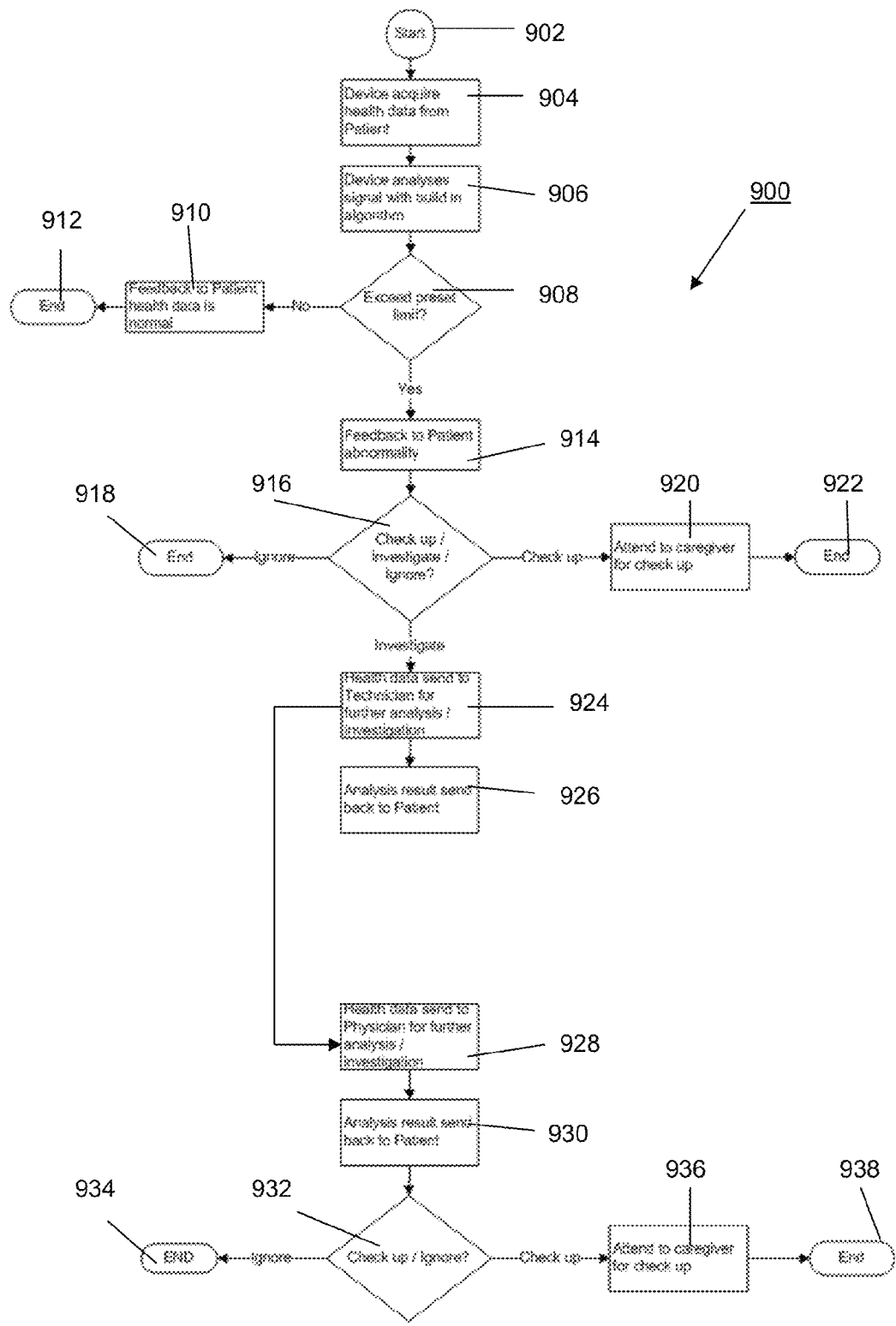
FIG. 9 is the flow chart showing how a system provides feedback based on the analysis of the health data of the patient.

FIG. 9 is the flow chart 900 showing how a system provides feedback based on the analysis of the health data of the patient. If there is any abnormality in the health data of the patient, the patient will be advised to take the necessary steps to improve his health condition, such as going for check-up or investigation, or sending health data to technician or physician for further analysis and investigation. In a preferred embodiment of the present invention, the system is a web-based application which allows the patient to view, manage and archive health data.

Processing commences in step 902.

In step 904, the network device 110 receives health data in a preferred embodiment of the present invention. The health data is transmitted from the server 116 to the network device 110 over local and/or wide area network or internet 114. The health data containing the feedback and diagnosis by the physician is displayed to the patient 102 on a display screen on the network device 110. The health data enables the patient to understand his health condition better and also to be aware of the physician's instructions regarding the necessary steps to take to improve his health condition.

In step 906, the network device 110 including a pre-installed analysis tool program, which conduct an analysis on the health data in a preferred embodiment of the present invention. The health data is sometimes known as signal. The analysis tool program may contain build-in algorithms (which is described in detail earlier) to conduct an analysis on the health data.

In step 908, the analysis tool program conducts a check if the health data exceed a certain limit in a preferred embodiment of the present invention.

If the health data do not exceed a limit, the analysis tool program produces a feedback report informing the patient that the health data is normal and that his health condition is healthy in step 910 and the processing end in step 912.

If the health data exceed a limit, the analysis tool program produces a feedback report informing the patient that the health data is not normal in step 914 and that necessary actions and steps have to be taken to improve his health condition. The necessary actions and steps include going for either a medical check-up or an investigation in step 916.

If the patient ignores the medical check-up or investigation, the processing ends in step 918. Otherwise, the patient can go to the caregiver for a medical check-up in step 920 where the patient will be given the necessary remedy to his health condition and the process subsequently ends in step 922.

If the patient does not want to go for a check-up, the patient can go for investigation in step 924 instead.

In step 924, the health data is sent to the technician for analysis and investigation. The completed analysis result will then be sent back to the patient in step 926.

If the technician discovers that the health data require further analysis and investigation, the health data will be sent to the physician for a further analysis and investigation in step 928. The completed analysis result will then be sent back to the patient in step 930. The completed analysis results usually contain advice from physician to go for a medical check-up.

In step 932, the patient has the option to follow the physician's advice to go for a medical check-up or not. If the patient ignores the physician's advice, the processing ends in step 934. Otherwise, the patient can go to the caregiver for a medical check-up in step 936 where the patient will be given be necessary remedy to his health condition and the process subsequently ends in step 938.

While the invention has been particularly shown and described with respect to a preferred embodiment thereof, it will be understood by those in the art that various changes in form and details can be made therein without departing from the spirit and scope of the invention.

The invention claimed is:

1. A system for facilitating medical diagnosis and consultation of heart disease for a patient, the system comprising:
   a diagnostic device comprising an interface unit having a display and a plurality of sensors, the diagnostic device configured for performing Electrocardiography on the patient, the diagnostic device further configured for processing a first diagnostic data and a second diagnostic data associated with the plurality of sensors, wherein said diagnostic device is flashed with a unique identifier suitable to act as a hardware security lock;
   a network device in communication with the diagnostic device and a remote server, the remote server for storing the first diagnostic data, the first diagnostic data to be based on for providing a metadata, wherein the metadata is transmitted to the network device;
   a software program pre-installed in the network device for detecting an abnormal event in the second diagnostic data, the abnormal event comprising the difference between the metadata and the second diagnostic data exceeds a preset limit,
wherein a signal is generated by the network device to send the second diagnostic data to the server upon the occurrence of the abnormal event.

2. The system according to claim 1, wherein the interface unit comprises a compact, consolidated circuit board unifying a plurality of processing circuitry.

3. The system according to claim 1, wherein the communication is wireless.

4. The system according to claim 1, wherein the communication is wired.

5. The system according to claim 4, wherein the communication link is a USB connection.

6. The system according to claim 1, wherein the server comprises application software programs, database and analysis tool programs configured for determining the patient's health condition by a physician.

7. The system according to claim 1, wherein the first diagnostic data comprises a first plurality of diagnostic data acquired by the diagnostic device prior to the second diagnostic data.

8. The system according to claim 1, wherein the second diagnostic data comprises a second plurality of diagnostic data acquired by the diagnostic device subsequent to the first diagnostic data.

9. The system according to claim 1, wherein the metadata is provided by a physician.

10. A method for facilitating remote medical diagnosis and consultation of heart disease for a patient, the method comprising:
performing Electrocardiography on the patient by a diagnostic device, the diagnostic device comprising an interface unit having a display and a plurality of sensors, the diagnostic device further configured for processing a first diagnostic data and a second diagnostic data associated with the plurality of sensors, wherein said diagnostic device is flashed with a unique identifier suitable to act as a hardware security lock;
allowing the communication of a network device with the diagnostic device and a remote server;
storing the first diagnostic data in the remote server;
defining a set of metadata based on the first diagnostic data;
transmitting the set of metadata to the network device;
detecting an abnormal event in the second diagnostic data by a software program pre-installed in the network device, the abnormal event comprising the difference between the second diagnostic data and the metadata exceeds a preset limit; and
generating a signal by the network device to send the second diagnostic data to the server upon the occurrence of the abnormal event.

11. The method according to claim 10, wherein performing Electrocardiography on the patient comprises:
pasting a plurality of leads on patient;
activating a reminder signal if at least one of the plurality of leads is not detected by the diagnostic device; and
gathering the diagnostic data when the plurality of leads is detected by the diagnostic device.

12. The method according to claim 10, wherein defining the metadata with the first diagnostic data comprises:
analyzing the first diagnostic data by a physician at the remote server, and
determining the metadata by the physician,
wherein the metadata is transmitted from the remote server to the network device.

13. The method according to claim 10, wherein the first diagnostic data comprises a first plurality of diagnostic data acquired by the diagnostic device prior to the second diagnostic data.

14. The method according to claim 10, wherein the second diagnostic data comprises a second plurality of diagnostic data acquired by the diagnostic device subsequent to the first diagnostic data.

* * * * *